United States Patent [19]

Weber-Unger

[11] Patent Number: 5,551,092
[45] Date of Patent: Sep. 3, 1996

[54] CLOSING APPARATUS FOR POCKETS IN ARTICLES OF CLOTHING

[75] Inventor: Georg Weber-Unger, Kufstein, Austria

[73] Assignee: Helbig GmbH & Co. Orthopädische Produkte KG, Brannenburg, Germany

[21] Appl. No.: 317,929

[22] Filed: Oct. 4, 1994

[30] Foreign Application Priority Data

Oct. 5, 1993 [DE] Germany ............................ 9315100 U

[51] Int. Cl.⁶ ............................... A41D 27/20; A41C 3/12
[52] U.S. Cl. ..................................... 2/247; 2/250; 450/31; 450/32; 450/92
[58] Field of Search .................... 2/73, 67, 247, 2/248, 249, 250, 251, 252; 450/30, 31, 32, 36, 53, 54, 55, 56, 57, 92; 150/143, 144, 149, 152

[56] References Cited

U.S. PATENT DOCUMENTS

| 458,235 | 8/1891 | Lieker | 150/152 X |
|---|---|---|---|
| 939,673 | 11/1909 | Cummings et al. | 150/149 |
| 1,824,354 | 9/1931 | Kotlicke | 150/152 |
| 2,124,287 | 7/1938 | Claviez | 150/152 |
| 2,788,042 | 4/1957 | Carden | 150/152 X |
| 3,348,241 | 10/1967 | Dodds | 450/54 X |
| 4,166,471 | 9/1979 | Griffen et al. | 450/56 X |
| 4,781,650 | 11/1988 | Budd | 450/56 X |
| 5,334,082 | 8/1994 | Barker | 450/32 X |

FOREIGN PATENT DOCUMENTS

| 8126663 | 1/1982 | Germany . |
|---|---|---|
| 9113346 | 3/1982 | Germany . |
| 3305096 | 8/1984 | Germany . |
| 8526268 | 12/1985 | Germany . |

Primary Examiner—Jeanette E. Chapman
Attorney, Agent, or Firm—Henry M. Feiereisen

[57] ABSTRACT

A closing apparatus for pockets in articles of clothing includes a soft, bendable, thin and flat body member which is securable to a garment and is comprised of at least three body sections, wherein each body section has two side parts, with one side part overlapping a side part of a neighboring body section, and with the other side part extending underneath a side part of another neighboring body section. A seam is applied about the perimeter of the body member for joining the body sections with each other in the respective overlapping areas. Each body section has a rectilinear edge which loosely sits upon the side part of a neighboring body section for closing the pocket of the garment and is displaceable for allowing access to the pocket. The loose edges intersect in a point of intersection which lies essentially in a center of the body member.

8 Claims, 1 Drawing Sheet

CLOSING APPARATUS FOR POCKETS IN ARTICLES OF CLOTHING

BACKGROUND OF THE INVENTION

The present invention refers to a apparatus for closing pockets in articles of clothing.

A closing apparatus is known which is used for closing a pocket e.g. of a prosthetic bra in order to retain a breast prosthesis received in the cup of the bra and to create a skin-friendly separation of the rear of the prosthesis and the wearer's body. The closing apparatus includes a body member of a soft, bendable, thin and flat material which is sewed to the perimeter of the bra cup at the side facing the wearer's body and is made of two body sections. Each body section has a side part which overlaps the side part of the other section and has an edge which is partially secured to the side part of the other body section and partially sits loosely upon the side part of the other body section, with the loose edge areas extending rectilinear and parallel to each other. In order to place or remove a prosthesis into or from the pocket, both loose edge areas are pushed apart by hand to form a slotted opening through which the prosthesis is inserted or removed.

Since shapes and sizes of prostheses differ widely among each other, the placement of the prosthesis through the slotted opening of the closing apparatus may pose problems with some breast prostheses, especially with those having lateral wings or those being of great size. The insertion or removal of such prostheses through the slotted opening becomes more difficult than e.g. a small prostheses with a circular base.

SUMMARY OF THE INVENTION

It is an object of the present invention to provide an improved closing apparatus for pockets in garments, obviating the afore-stated drawbacks.

In particular it is an object of the present invention to provide an improved closing apparatus which allows formation of an opening of variable configuration and size, and yet ensures a secure closing of the pocket.

These objects and others which will become apparent hereinafter are attained in accordance with the present invention by providing the body member with at least three body sections, each of which having two side parts, with one side part overlapping a side part of a first neighboring body section and with the other side part extending underneath a side part of a second neighboring body section, and by joining overlapping side parts of neighboring body section along a first edge area of the side parts, with each side part having a second edge area sitting loosely on a side part of a neighboring body section in the closed configuration of the pocket, wherein the loose second edge areas of the side parts intersect in a point of intersection which lies essentially in a center of the body member.

The closing apparatus according to the present invention has the advantage that the opening which is formed through pushing the side parts apart can assume almost any shape at maximum size. Thus, the possibilities for use of this closing apparatus are greatly expanded. For example, the closing apparatus according to the present invention may be applicable for use in all kinds of garments such as pockets of trousers or jackets.

Preferably, the loose edge areas of each body section extend rectilinearly to simplify the manufacture of the body sections.

According to another feature of the present invention, each body section is of double-ply material and folded along the loose edge areas to effect a superior restoring capability of the body sections and a stable closing of the body sections.

The closing apparatus according to the present invention can be used for a prosthetic pocket to receive a breast prosthesis. In this case, the prosthetic pocket together with the breast prosthesis is placed in the cup of a bra. When the prosthetic pocket is provided with a closing apparatus according to the present invention, the body member is secured to the perimeter of the pocket facing the wearer's body.

In addition, the closing apparatus may also find application in a bathing suit for wearers of a prosthesis, by securing the body member at the side facing the wearer's body to the perimeter of the cup of the bra in which the breast prosthesis is received.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
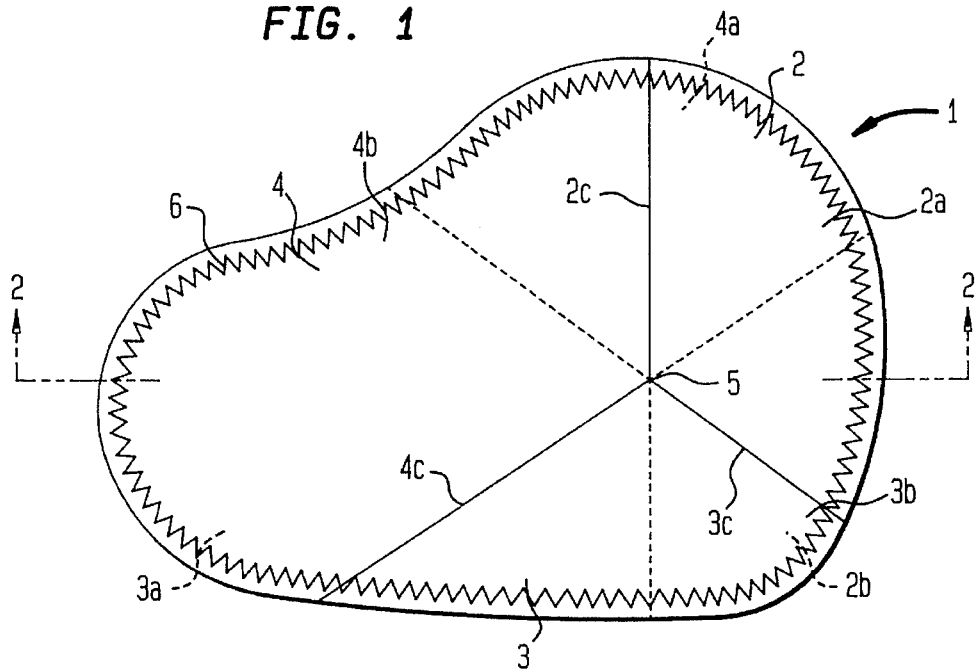
FIG. 1 is a schematic top view of a closing apparatus according to the present invention, for use in an exemplified prosthetic bra.

Throughout all the Figures, the same or corresponding elements are always indicated by the same reference numerals.

Turning now to the drawing, and in particular to FIG. 1, there is shown a schematic top view of a apparatus according to the present invention, for closing a pocket of a prosthetic bra which is shown by way of example only. The closing apparatus includes a body member 1 which is comprised of three body sections 2, 3, 4 of textile material, e.g. cotton. Each body section 2, 3, 4 has two side parts 2a, 2b; 3a, 3b; 4a, 4b, with one side part overlapping a side part of a neighboring body section and the other side part extending underneath a side part of the other neighboring body section. Thus, the body section 2 has a side part 2a, which overlaps the side part 4a of the body section 4, and a side part 2b which extends underneath the side part 3b of the body section 3 while the other side part 3a of the body section 3 extends underneath the side part 4b of the body section 4.

Each side part 2a, 2b, 3a, 3b, 4a, 4b has a rectilinear edge 2c, 3c, 4c which sits loosely upon the neighboring body section when the pocket is closed. The edges 2c, 3c, 4c intersect in a point of intersection 5 which essentially lies in the center of the body member 1. The edge 2c of body section 2 overlaps the body section 4 in the area extending from its upper end in FIG. 1 to the point of intersection 5 and lies underneath the body section 3 in the area extending from the point of intersection 5 to its lower end in FIG. 1. The edge 3c of body section 3 overlaps the body section 2 in the area extending from its lower right hand end in FIG. 1 to the point of intersection 5 and lies underneath the body section 4 in the area extending from the point of intersection 5 to its upper left hand end in FIG. 1. The edge 4c of body section 4 overlaps the body section 3 in the area extending from its lower left hand end in FIG. 1 to the point of intersection 5 and lies underneath the body section 2 in the area extending from the point of intersection 5 to its upper right hand end in FIG. 1.

A peripheral seam 6 is applied about the perimeter of the body member 1 or along a first edge area of each side part of each body section to and join the body sections 2, 3, 4 with each other in the respective overlap areas. In particular, as shown in FIG. 1, the seam 6 connects the body section 2 with the body section 4 in the area between the upper right hand end of the edge 4c and the upper end of the edge 2c. Further, the seam 6 connects the body section 4 with the body section 3 in the area between the upper left hand end of the edge 3c and the lower left hand end of the edge 4c, and connects the body section 3 with the body section 2 in the area between the lower end of the edge 2c and the lower right hand end of the edge 3c.

Figure 2:
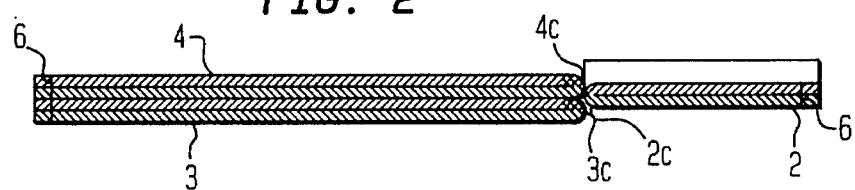
FIG. 2 is a sectional view of the closing apparatus taken along the line II—II in FIG. 1.

As shown in particular in FIG. 2, which is a sectional view of the closing apparatus taken along the line II—II in FIG. 1, the body sections 2, 3, 4 am each made of double-ply material such as textile material like cotton, and are folded along their respective edges 2c, 3c, 4c. Both layers of each body section 2, 3, 4 are joined together about their perimeter by the peripheral seam 6.

Figure 3:
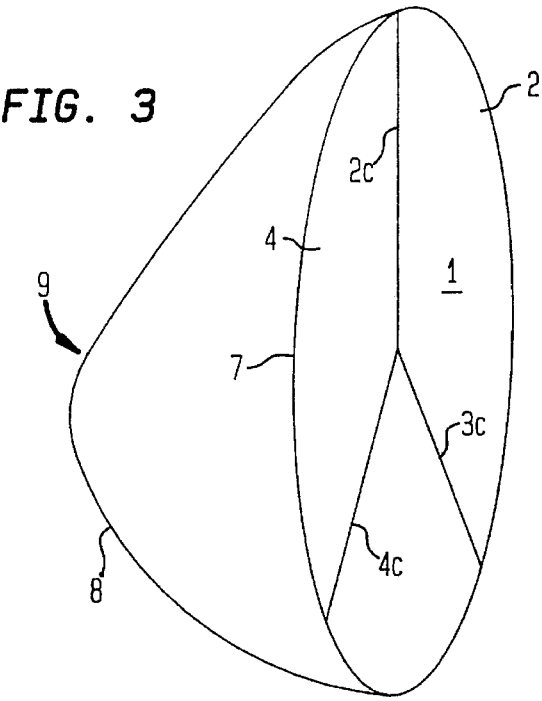
FIG. 3 is a schematic perspective illustration of an exemplified prosthetic bra, with the closing apparatus being attached to a cup of the prosthetic bra.

Turning now to FIG. 3, there is shown a schematic perspective illustration of an exemplified prosthetic bra 9 which is equipped with a the closing apparatus according to the present invention, with the body member 2 being secured to a cup 8 of the prosthetic bra 9 along the perimeter area facing the wearer's body. By pushing the rectilinear edges 2c, 3c, 4c apart, an opening is formed through which a breast prosthesis can be placed into the cup 8 or removed therefrom. After release, the body sections 2, 3, 4 essentially return automatically into the position shown in FIG. 3 for closing the pocket formed by the cup 8 so that the prosthesis is securely retained therein. The body member 1 thus forms a skin-friendly partition between the prosthesis and the wearer's body.

When the pocket is closed by the body member 1, the edges 2c, 3c, 4c form a star-like configuration which creates an opening of random shape and allows maximum size, reaching almost to the outer boundery of the body member 1. Thus, the insertion and placement as well as removal of a prosthesis into or from the cup 8 are effected in a convenient and simple manner even in cases in which the prosthesis is of relative large size and of a base that greatly deviates from a circular configuration.

While the invention has been illustrated and described as embodied in a closing apparatus for pockets in articles of clothing, it is not intended to be limited to the details shown since various modifications and structural changes may be made without departing in any way from the spirit of the present invention.

What is claimed as new and desired to be protected by Letters Patent is set forth in the appended claims:

We claim:

1. A closing apparatus for pockets in articles of clothing; comprising:

a body member which is securable to an article of clothing and comprised of at least three body sections, each body section having two side pads, with one side pad overlapping a side pad of one neighboring body section and with the other side pad extending underneath a side pad of another neighboring body section; and sealing means for joining overlapping side pads of neighboring body sections along a first edge area of said side pads, each said side pad having a second edge area which loosely sits upon the side pad of a neighboring body section for effecting a closure of the pocket of the article of clothing and is movable away from the neighboring body section to allow access to the pocket, said second edge areas of said side parts intersecting in a point of intersection which lies essentially in a center of said body member.

2. The closing apparatus of claim 1 wherein said second edge areas of said body sections are of rectilinear configuration.

3. The closing apparatus of claim 1 wherein each body section is of double-ply material and folded along the second edge area.

4. The closing apparatus of claim 3 wherein said body member is made of soft bendable material and is of thin and flat configuration.

5. The closing apparatus of claim 1 wherein said body sections are made of a textile material.

6. The closing apparatus of claim 1 wherein said body member is secured to a prosthetic pocket of a breast prosthesis along a perimeter facing a wearer's body.

7. The closing apparatus of claim 1 wherein said body member is secured to a breast prosthesis, which receives a cup of a bra, along a perimeter facing a wearer's body.

8. The closing apparatus of claim 1 wherein said body member is secured to a breast prosthesis, which receives a cup of a bra of a bathing suit, along a perimeter facing a wearer's body.

\* \* \* \* \*

UNITED STATES PATENT AND TRADEMARK OFFICE
CERTIFICATE OF CORRECTION

PATENT NO. : 5,551,092
DATED : September 3, 1996
INVENTOR(S) : Georg Weber-Unger It is certified that error appears in the above-indentified patent and that said Letters Patent is hereby corrected as shown below:

column 3, line 9, amend -- or along a first edge area of each side part of each body section to-- column 3, line 23, change "am" to --are--.

column 4, lines 14 to 22, change "pad" to --part--.

Signed and Sealed this

Eighteenth Day of February, 1997

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,551,092
DATED      : September 3, 1996
INVENTOR(S) : Georg Weber-Unger It is certified that error appears in the above-indentified patent and that said Letters Patent is hereby corrected as shown below:

On title page, item [73], change "Helbig GmbH & Co. Orthopädische Produkte KG" to --Dr. Helbig GmbH & Co. Orthopädische Produkte KG--.

Signed and Sealed this

Twenty-second Day of April, 1997

Attest:

BRUCE LEHMAN

*Commissioner of Patents and Trademarks*

*Attesting Officer*